(12) United States Patent
Sakakura

(10) Patent No.: US 8,519,711 B2
(45) Date of Patent: Aug. 27, 2013

(54) MAGNETIC RESONANCE IMAGING APPARATUS

(75) Inventor: Yoshitomo Sakakura, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 509 days.

(21) Appl. No.: 12/751,531

(22) Filed: Mar. 31, 2010

(65) Prior Publication Data

US 2010/0244833 A1    Sep. 30, 2010

(30) Foreign Application Priority Data

Mar. 31, 2009 (JP) ................. 2009-087931

(51) Int. Cl.
*G01R 33/48* (2006.01)
*A61B 5/05* (2006.01)
*G01V 3/00* (2006.01)

(52) U.S. Cl.
USPC ............ 324/315; 324/309; 324/318; 600/412

(58) Field of Classification Search
USPC .................... 324/300–322; 600/407–464
See application file for complete search history.

(56) References Cited

U.S. PATENT DOCUMENTS

| | | | | |
|---|---|---|---|---|
| 6,615,069 | B1 * | 9/2003 | Komura et al. | 600/412 |
| 6,825,667 | B1 * | 11/2004 | Tsuda | 324/320 |
| 7,508,205 | B2 * | 3/2009 | Thelissen et al. | 324/307 |
| 7,602,185 | B2 * | 10/2009 | Nozaki | 324/315 |
| 7,706,856 | B2 * | 4/2010 | Dean et al. | 600/410 |
| 7,741,847 | B2 * | 6/2010 | Nakabayashi et al. | 324/320 |

FOREIGN PATENT DOCUMENTS

| | | |
|---|---|---|
| JP | 04-176440 | 6/1992 |
| JP | 06-292662 | 10/1994 |
| JP | 08-056917 | 3/1996 |
| JP | 09-262222 | 10/1997 |
| JP | 10-155766 | 6/1998 |
| JP | 11-076195 | 3/1999 |

* cited by examiner

*Primary Examiner* — Melissa Koval
*Assistant Examiner* — Emily Chan
(74) *Attorney, Agent, or Firm* — Oblon, Spivak, McClelland, Maier & Neustadt, L.L.P.

(57) ABSTRACT

In an MRI apparatus, a detecting unit that includes a thermographic imaging equipment and a normal imaging camera detects a change in temperature of an imaging space from outside of the imaging space. A judging unit judges whether the imaging space has a point at a temperature greater than a threshold TH, and if the judging unit judges the imaging space has such a point with a temperature greater than the threshold, the apparatus stops the sequence that applies a gradient magnetic field to the subject.

16 Claims, 8 Drawing Sheets

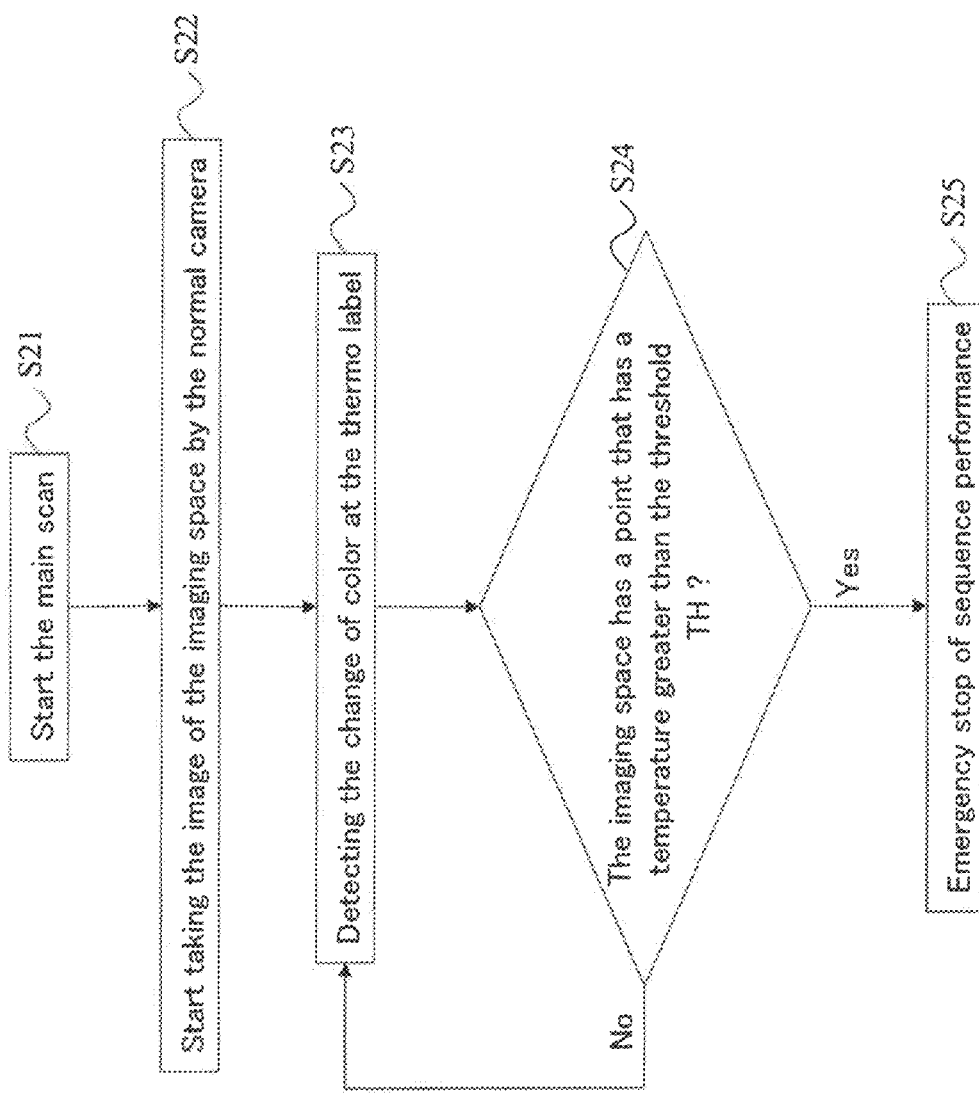

MAGNETIC RESONANCE IMAGING APPARATUS

CROSS-REFERENCE TO PRIORITY APPLICATIONS

This application is based upon and claims the benefit of priority from the prior Japanese Patent Application No. 2009-87931, filed Mar. 31, 2009, the entire contents of which are incorporated herein by reference.

BACKGROUND

1. Field

The present invention relates to magnetic resonance imaging apparatuses, and more particularly magnetic resonance imaging apparatuses that are able to detect the temperature of an imaging space from outside of the imaging space.

2. Description of Related Art

An MRI apparatus detects the radio-frequency signal (NMR signal) that comes from a subject (the patient) by NMR phenomenon. An MRI apparatus applies a gradient magnetic field to the subject to provide spatial information to the NMR signal.

The gradient magnetic field is generated by passing an electric current through a coil to generate the gradient magnetic field. This gradient coil is placed in the direction of the X-axis, Y-axis, and Z-axis in relation to the space coordinates of the subject.

This kind of gradient coil has a large electric current passed therethrough. Therefore, it is problem that the gradient coil develops high heat. Therefore, generally a device for cooling down the gradient coil is set up on the MRI apparatus. Additionally, it has been proposed to provide a temperature sensor that changes its resistance value with a change of temperature, for example a thermoelectric couple and a thermistor, to directly measure the temperature inside of the imaging space in which the gradient magnetic field and the subject are placed (see Jpn. Pat. App. KOKAI Publications No. 04-176440, No. 06-292662).

However, in the case of the related art, the thermoelectric couple and the thermistor detect the change in temperature based on the change in resistance. Therefore, it is necessary to pass an electric current through these sensors. In the case of an MRI apparatus, this electric current generates a noise. Also, in an MRI apparatus the trend of generating high heat on the gradient coils that are placed in the direction of the X-axis, Y-axis, and Z-axis by applying the gradient magnetic field results in a change in temperature at the inside of the imaging space varying through the imaging space. Therefore, a temperature sensor that detects a temperature at a specific point in an imaging space is not completely adapted to be used in an MRI apparatus. Also, a false operation of the temperature sensor and the main device of an MRI apparatus may result by setting up the temperature sensor in the imaging space in that a radio frequency pulse may be applied. Therefore, there are drawbacks with utilizing such a temperature sensor in an MRI apparatus.

For such reasons, the related art systems detecting the temperature in the imaging space may not adequately serve their purpose and may possibly not ensure the safety of the subject and the apparatus.

SUMMARY

In view of such circumstances, an object of the present invention is to enable to detect the temperature in the imaging space of an MRI or similar apparatus.

BRIEF DESCRIPTION OF THE DRAWINGS

The accompanying drawing, which are incorporated in and constitute a part of the specification, illustrate embodiments of the invention, and together with the general description given above and the detailed description of the embodiments given below, serve to explain the principles of the invention, in which:

FIG. 8 is a flowchart showing a process sequence of the MRI apparatus according to the second embodiment of the invention.

DETAILED DESCRIPTION

A magnetic resonance imaging apparatus (an MRI apparatus) according to an embodiment of the invention will now be explained with reference to the figures.

In the case of a first embodiment, aspects of scanning a change in temperature of the subject (the patient) and a change in temperature in an imaging space in a gantry by infrared thermographic imaging equipment are explained.

Figure 1:
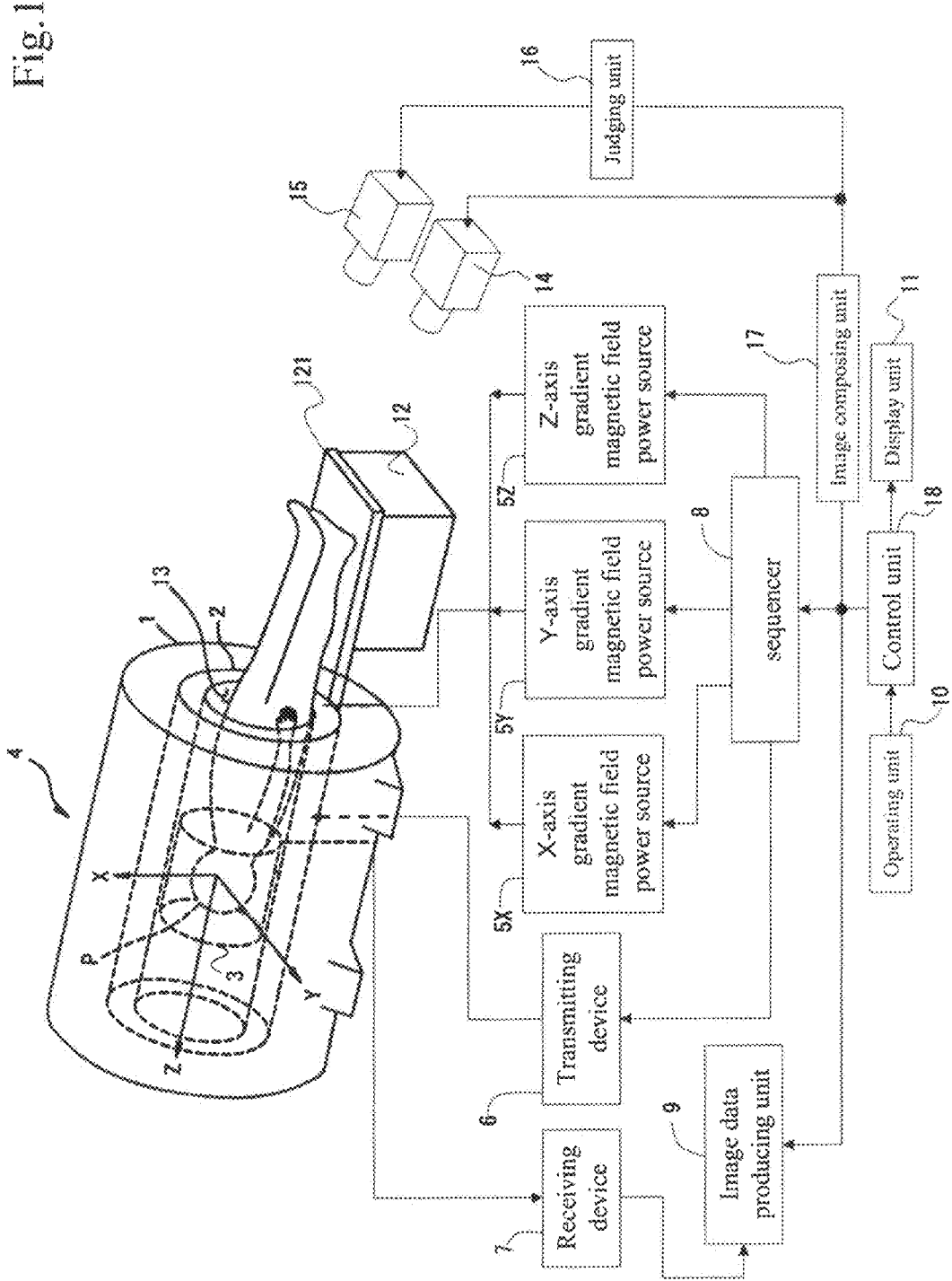
FIG. 1 is a block diagram showing a structure of an MRI apparatus according to a first embodiment of the invention.

At first, the composition of the MRI apparatus according to the first embodiment will be explained by referring to FIG. 1. FIG. 1 is a block diagram showing a structure of an MRI apparatus according to a first embodiment of the invention.

The MRI apparatus includes a magnet device 1 that generates a static magnetic field, a gradient coil 2 that generates a gradient magnetic field, and a transmitting coil 3 arranged in a gantry 4 in a concentric pattern.

The magnet device 1 is required to generate a static magnetic field of high magnetic field intensity, high uniformity, and high stability. Therefore, a superconducting magnet and a permanent magnet may be used as the magnet device 1. In the first embodiment, the MRI apparatus is explained supposing that the magnet device 1 includes a superconducting magnet.

The gradient coil 2 includes an X-axis gradient coil, a Y-axis gradient coil, and a Z-axis gradient coil. For driving these three gradient coils, the X-axis gradient coil, the Y-axis gradient coil, and the Z-axis gradient coil are respectively connected to an X-axis gradient magnetic field power source 5X, a Y-axis gradient magnetic field power source 5Y, and a Z-axis gradient magnetic field power source 5Z. The X-axis gradient magnetic field power source 5X, the Y-axis gradient magnetic field power source 5Y, and the Z-axis gradient magnetic field power source 5Z are placed outside of the gantry 4.

The transmitting coil (not shown in FIG. 1) is placed between an inside wall that is composed of the gantry 4 and the gradient coil 2, and the transmitting coil transmits a radiofrequency pulse to the subject P by a radiofrequency pulse current provided by the transmitting device 6.

The receiving coil 3 receives the nuclear magnetic signal generated from the subject P, and the receiving coil 3 provides the nuclear magnetic signal to the receiving device 7. The X-axis gradient magnetic field power source 5X, the Y-axis gradient magnetic field power source 5Y, the Z-axis gradient magnetic field power 5Z source, and the transmitting device 6 are controlled in accordance with a predefined pulse sequence that is programmed preliminarily by sequencer 8. The X-axis gradient magnetic field power source 5X, the Y-axis gradient magnetic field power source 5Y, the Z-axis gradient magnetic field power source 5Z, and the transmitting device 6 generate a gradient magnetic field in the X-axis direction, a gradient magnetic field in the Y-axis direction, a gradient magnetic field in the Z-axis direction, and the radio frequency pulse current.

The MRI apparatus also includes an image data producing unit 9 that reconstructs the MR signal provided from the receiving unit 7 and produces image data, an operating unit 10 that performs a choice of category of the image, the way to take the image, and settings of the parameters for taking the image, and a display unit 11 that chooses one or more image data produced by the image data producing unit 9 and displays such on a screen.

Subject P is placed on a table top 121 supported by a bed device 12 and subject P is inserted into the imaging space 13 as an imaging area in the gantry 4. The imaging space 13 includes the inner wall of the gantry 4.

A normal imaging camera 14 is placed at the sidewall in the examination room and the normal camera 14 takes an image of the imaging space 13 preliminarily. The image that is taken by the normal camera 14 is input to the image composing unit 17.

A thermographic imaging equipment 15 takes an image data in which the image color is varied by change in temperature, and outputs the thermographic image data. The thermographic imaging equipment 15 can be placed at the sidewall in the examination room. The image taken by the thermographic imaging equipment 15 is input to judging unit 16 and image composing unit 17.

To take an image data that an operator is able to recognize, a direction of taking an image and an imaging area of the normal camera 14 and the thermographic imaging equipment 15 are set. The direction of taking an image and the imaging area of the normal camera 14 and the thermographic imaging equipment 15 are not limited to any specific direction.

Judging unit 16 detects a change in temperature of imaging space 13 including the subject P based on the image data transmitted by the thermographic imaging equipment 15. The judging unit 16 compares the change in temperature of the imaging space 13 to a threshold TH set preliminarily, and the judging unit 16 judges whether the imaging space 13 has a point at a temperature greater than the threshold TH.

An example of the way the judging unit 16 performs its judging operation will be explained by referring to FIG. 2 and FIG. 3.

Figure 2:
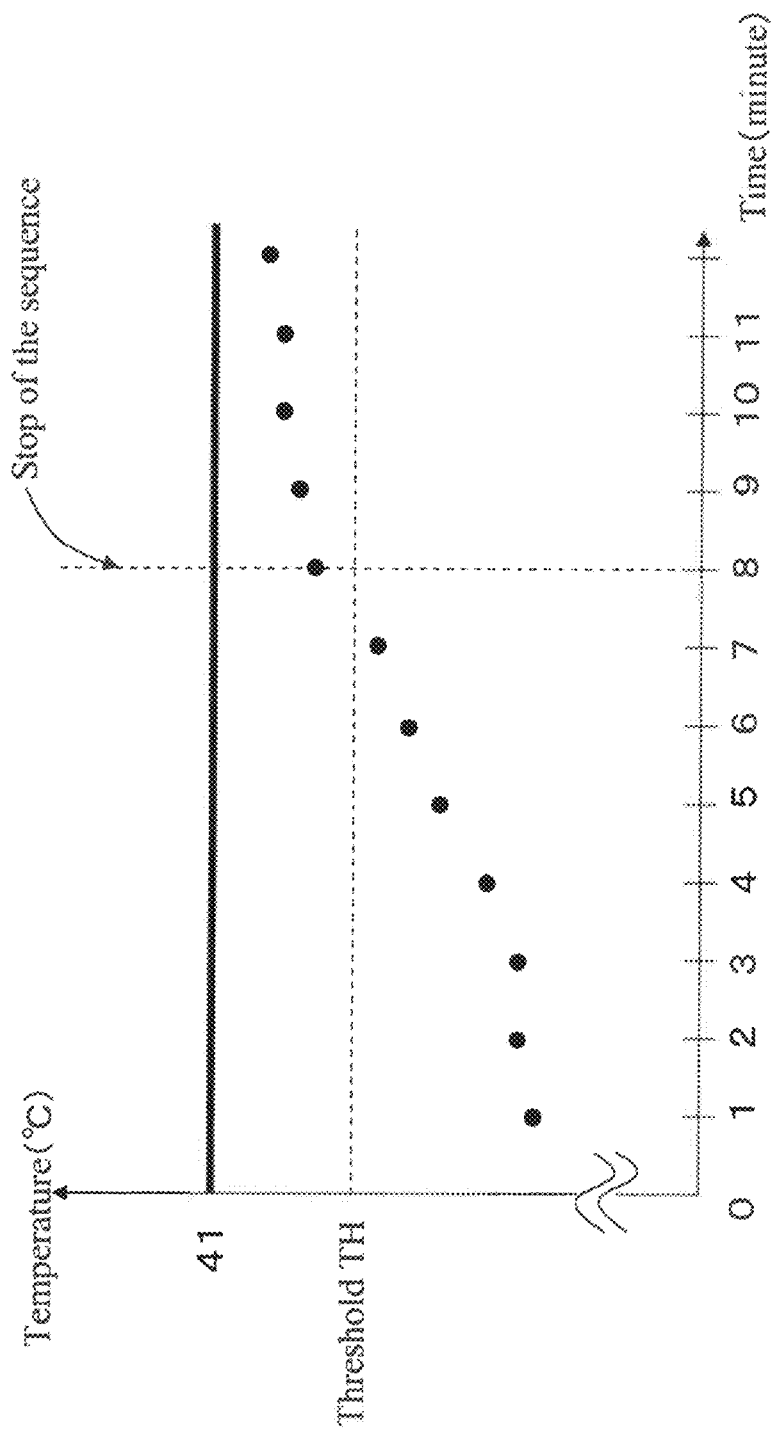
FIG. 2 is an example of a graph showing a highest temperature in an imaging space by taking a sample from an image by a thermographic imaging equipment in chronological order of an operation of a judging unit of an MRI apparatus according to the first embodiment of the invention.
Figure 3:
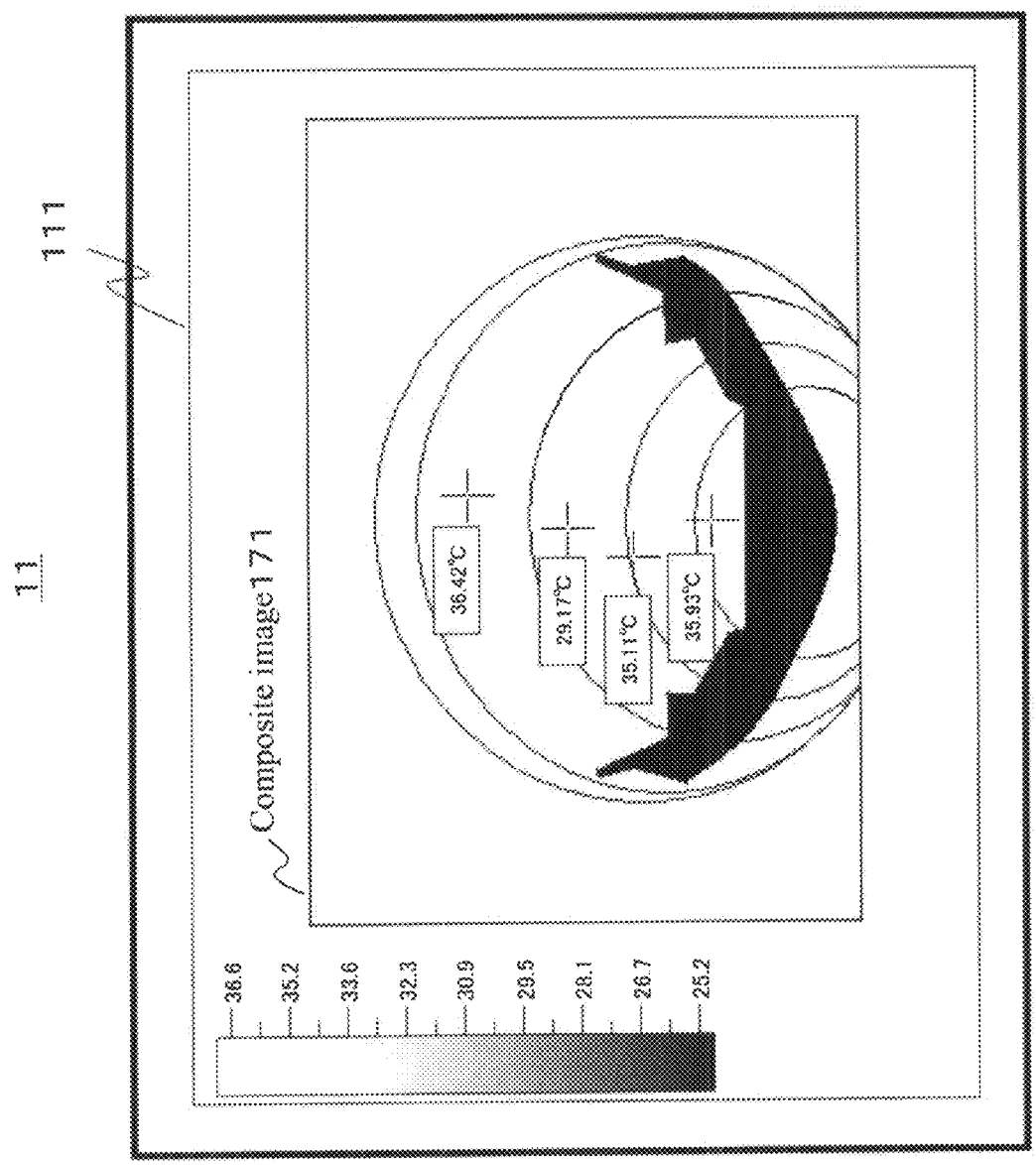
FIG. 3 is an example showing a composite image formed by combining images by thermographic imaging equipment and a normal camera according to the first embodiment of the invention.

FIG. 2 is an example of a graph showing the highest temperature in the imaging space 13 by taking a sample from the image by the thermographic imaging equipment 15 in chronological order at predetermined intervals, for example every minute, and that are provided to the judging unit 16 of the MRI apparatus according to a first embodiment of the invention. FIG. 3 is an example showing a composite image formed by combining the images from the thermographic imaging equipment 15 and the normal camera 14 according to the first embodiment of the invention, and which is displayed on a display screen 111 of the display unit 11.

For example, judging unit 16 takes a highest temperature sample from the change in temperature shown in the image taken every one minute by the thermographic imaging equipment 15, and the judging unit 16 compares the highest temperature sample to the threshold TH. In FIG. 2, the highest temperature sample from the change in temperature shown in the image and exceeding the threshold TH is taken eight minutes after the start of imaging by the thermographic imaging equipment 15. In that case, the judging unit 16 informs that situation to control unit 18, and the control unit 18 directs sequencer 8 to stop the sequence when the detected temperature exceeds the threshold TH.

As for a way to inform an operator of the stopping of the sequence, an alarm may be sounded and an alarm display may be displayed on the display screen 111 of the display unit 11.

The change in temperature of imaging space 13 is affected by the difference between the driving of the X-axis gradient coil, the Y-axis gradient coil, and the Z-axis gradient coil. Therefore, the judging unit 16 can take a highest temperature sample from the change in temperature shown in the image taken by the thermographic imaging equipment 15 in a limited area based on the pulse sequence to control the drive of the three gradient coils. For example, in the case that the apparatus drives only the X-axis gradient coil on both sides of the subject P placed into the X-axis direction on the bed device 12, the judging unit 16 can take a highest temperature sample from the change in temperature shown in the image taken by the thermographic imaging equipment 15 in the limited area corresponding to the position at which the X-axis gradient coil is set. In this way, the judging unit 16 may be able to take a highest temperature sample more efficiently.

The image composing unit 17 combines the images by the thermographic imaging equipment 15 and the normal camera 14 and inputs the composite image 171 (of FIG. 3) to the display unit 11. As shown in FIG. 3, the display unit 11 displays the composite image 171 on the display screen 111 for the operator to recognize the change in temperature of the imaging space 13.

According to a regulation of the International Electrotechnical Commission, the apparatus may set the threshold TH for 41 degrees Celsius or less as the temperature in the imaging space 13 is not to exceed 41 degrees Celsius.

Additionally, the MRI apparatus according to the first embodiment of the invention includes the control unit 18 to perform overall control with respect to each unit.

Regarding the MRI apparatus composed as above, the sequences to detect the change in temperature of the imaging space 13 including the subject P will be explained referring to FIG. 1 through FIG. 4.

Figure 4:
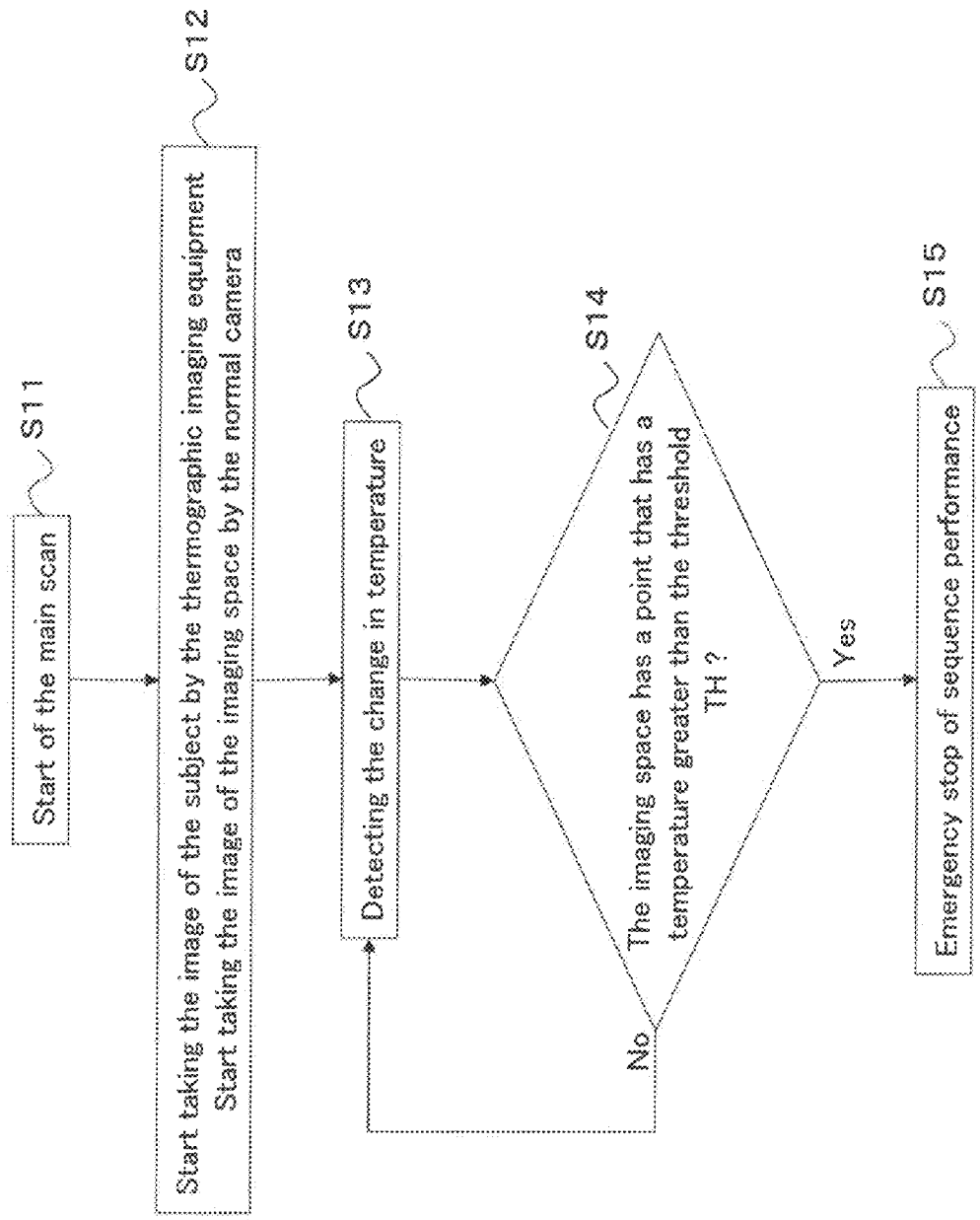
FIG. 4 is a flowchart showing a process sequence of the MRI apparatus according to the first embodiment of the invention.

FIG. 4 is a flowchart showing process sequence of the MRI apparatus according to a first embodiment of the invention;

In Step S11 in FIG. 4, the operator slides the tabletop 121 of the bed device 12 that has the subject P into the imaging space 13 and places the imaging point of the subject P to a predetermined position in the scanning field. The operator directs the control unit 18 to start the main scanning by operating unit 10. The control unit 18 directs each unit to start the main scanning based on the settings, the apparatus scanning a desired cross section in the scanning field. The image data producing unit 9 reconstructs the MR signal and produces the image data. By repeating this sequence, the desired cross section image data are produced in a designated scanning point of the subject P.

In Step S12 in FIG. 4, the thermographic imaging equipment 15 starts scanning the imaging space 13 including the subject P, when the main scanning starts. The thermographic imaging equipment 15 inputs the thermographic image to the judging unit 16. The normal camera 14 may be different from the thermographic imaging equipment 15 and may take an image at any time regardless of the main scanning.

In Step S13 in FIG. 4, the judging unit 16 detects the change in temperature of the imaging space 13 including the subject P based on the image transmitted by the thermographic imaging equipment 15.

In Step S14 in FIG. 4, the judging unit 16 compares the change in temperature in the imaging space 13 to the threshold TH set preliminarily and the judging unit 16 judges whether the imaging space 13 has a point at a temperature greater than the threshold TH.

In Step S15 in FIG. 4, in the case that the judging unit 16 judges the imaging space 13 has a point at a temperature greater than the threshold TH (if Yes in Step S14), the control unit 18 directs the sequencer 8 to stop the sequence. The sequencer 8 stops the sequence based on the direction that the control unit 18 transmitted.

According to the first embodiment of the invention, it is possible to detect a change in temperature of the imaging space 13 of an MRI apparatus.

According to the first embodiment of the invention, it is possible to detect the change in temperature of the imaging space 13 that the subject may touch and the change in temperature of the subject at the same time, and thereby the operator can recognize the condition of the subject P by the thermographic imaging equipment 15.

It is also possible to prevent strain and blurring of the image with the change of the static magnetic field intensity caused by the change of temperature occurring by monitoring the change in temperature of the imaging space 13 and it is possible to improve the efficiency in the examination.

By taking a highest temperature sample from the change in temperature shown in the image taken by the thermographic imaging equipment 15 in the limited area based on the pulse sequence to control the drive of the three gradient coils, the judging unit 16 is also able to take a highest temperature sample more efficiently.

The invention is not limited to the above first embodiment as modifications to components are possible. For example, modifications can be made by combining components shown in the above embodiment. It may also be possible to delete some components from the components shown in the above embodiment. Additionally, components in different embodiments may be able to be combined.

In the first embodiment, the thermographic imaging equipment 15 is used for detecting a change in temperature of the imaging space 13, but detecting the change in temperature of the imaging space 13 is not limited to using the thermographic imaging equipment 15. Another device instead of the thermographic imaging equipment 15 could be utilized that can obtain a temperature of a large area including the subject spacing area 13 from outside of the subject spacing area 13.

In the first embodiment, the judging unit 16 compares the change in temperature of the imaging space 13 to the threshold TH set preliminarily and the judging unit 16 judges whether the imaging space 13 has a point at a temperature greater than threshold TH. In the case the judging unit 16 judges the imaging space 13 has a point at a temperature greater than threshold TH, the sequencer 8 stops the sequence. This embodiment can, however, operate to only obtain the information about the change in temperature of the imaging space 13 from outside of subject spacing area 13, for example using the thermographic imaging equipment 15, and to transmit the information to the operator, and then allow the operator to perform a subsequent control. It is not necessary to both judge the temperature of imaging space 13 by judging unit 16 and then to control the automatic stopping of the sequence.

In the above embodiment, the judging unit 16 detects the highest temperature change in the imaging space 13 including the subject P and compares the change in temperature of the imaging space 13 to the threshold TH set preliminarily, and the judging unit 16 judges whether the imaging space 13 has a point at a temperature greater than threshold TH. But the way to perform the judging is not limited to that operation. Various ways to perform the judging could be implemented.

Another way to perform the judging is now explained with reference to FIG. 5 and FIG. 6.

Figure 5:
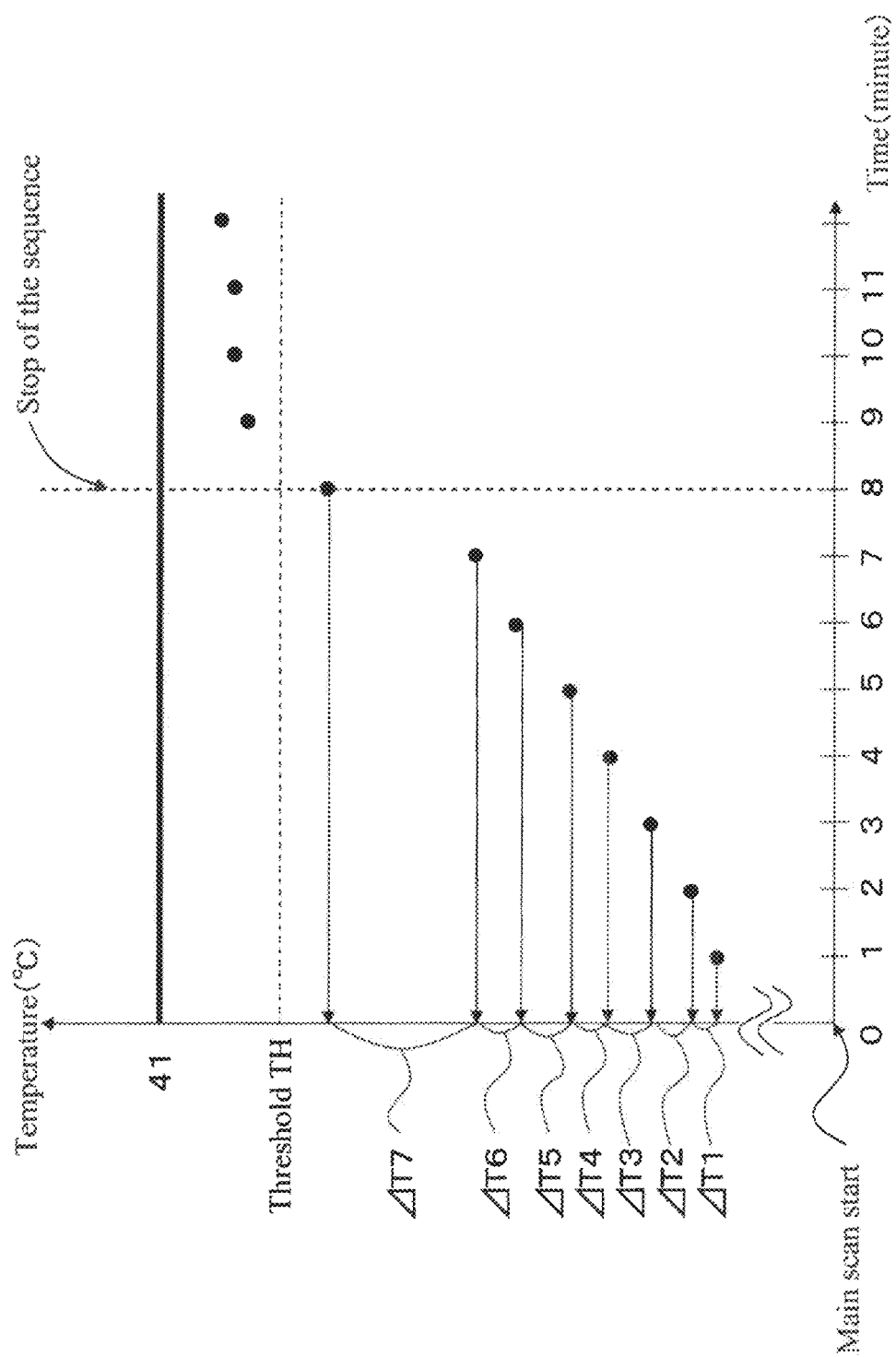
FIG. 5 is another example of a graph showing a highest temperature in the imaging space by taking a sample from the image by the thermographic imaging equipment in chronological order of the operation of the judging unit of an MRI apparatus according to the first embodiment of the invention.
Figure 6:
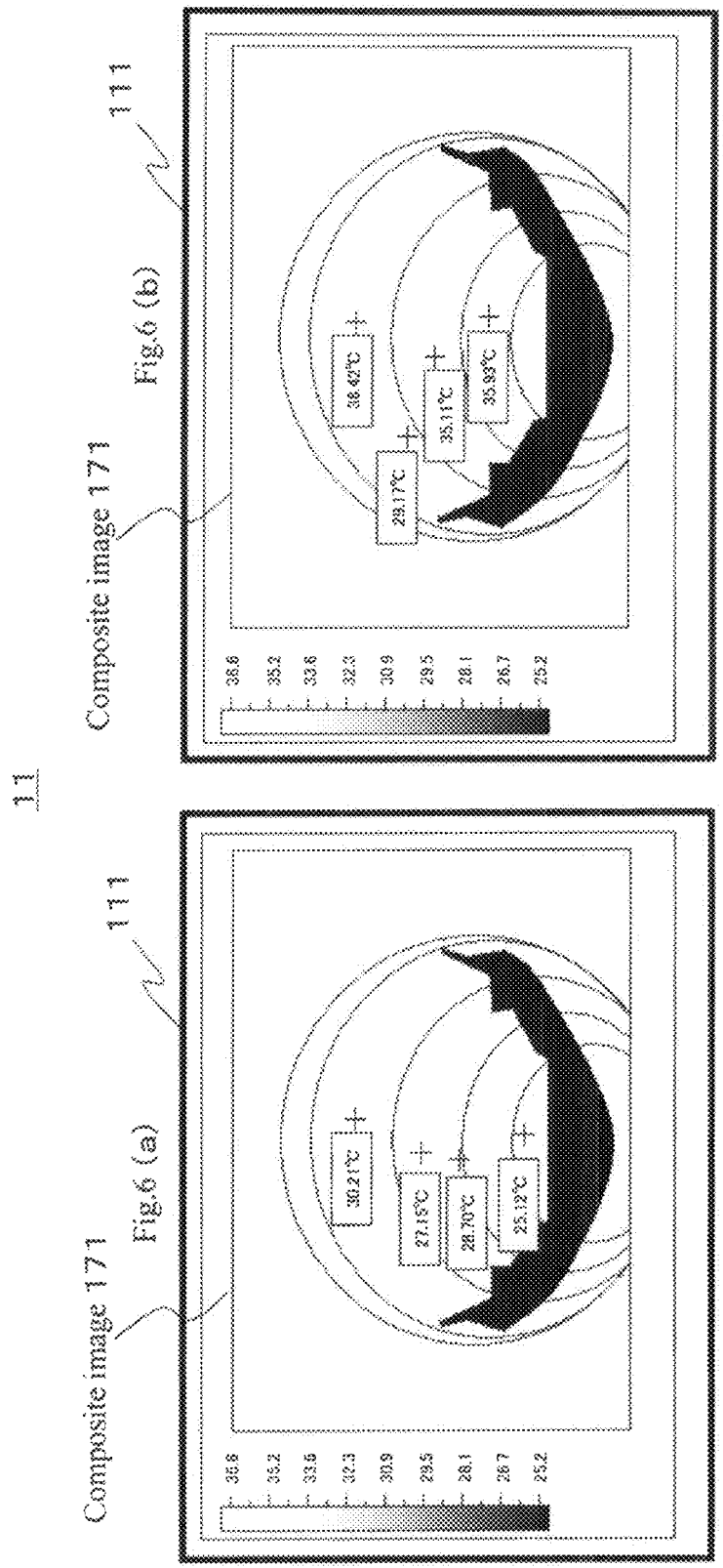
FIGS. 6(a) and 6(b) are an example showing composite images formed by combining images by thermographic imaging equipment and a normal camera according to the first embodiment of the invention.

FIG. 5 is an example of a graph showing a highest temperature in the imaging space obtained by taking a sample from the image by the thermographic imaging equipment 15 in chronological order at predetermined intervals, and provided to the judging unit 16, of an MRI apparatus according to a modified or further embodiment of the invention. FIGS. 6(*a*) and 6(*b*) are examples showing the composite images formed by combining the images by the thermographic imaging equipment 15 and the normal camera 14 according to the modified or further embodiment of the invention. In FIG. 6(*a*), the composite image 171 shows the condition of the imaging space 13 in the first seven minutes after a main scanning start. In FIG. 6(*b*), the composite image 171 shows the condition of the imaging space 13 in the first eight minutes after the main scanning start.

In this further example, the judging unit 16 takes a highest temperature sample from the change in temperature shown in the image taken every one minute, for example, by the thermographic imaging equipment 15. The judging unit 16 calculates the difference value between every highest temperature, and does not directly compare the highest temperature sample to the threshold TH (see the difference values $\Delta T1 \sim \Delta T7$ in FIG. 5).

When the difference value $\Delta T$ exceeds a predefined difference threshold, the control unit 18 directs the sequencer 8 to stop the sequence. In FIG. 5, in the case that the difference value between two highest temperature shown in the images taken by the thermographic imaging equipment 15 in the seven and eight minutes after main scanning exceeds the predefined threshold, the judging unit 16 transmits the information to the control unit 18 and the control unit 18 directs the sequencer 8 to stop the sequence.

The image composing unit 17 combines the images by the normal camera 14 and the thermographic imaging equipment 15. As shown in FIGS. 6(*a*) and 6(*b*), the display unit 11 displays the composite images 171 on the display screen 111 for the operator to recognize the change in temperature of the imaging space 13.

The judging unit 16 performs the judging based on the information taken at the different times. Therefore, it is easy for the operator to compare two changes in temperature by showing two images that are taken at the different times from each other as a stop motion.

According to the above judgment, the MRI apparatus is able to detect that the highest temperature on the change in temperature of the imaging space 13 rises rapidly. As shown in FIG. 5, the MRI apparatus stops the sequence before the highest temperature exceeds the threshold TH, and thereby it is possible to prevent the highest temperature of the imaging space 13 from exceeding the threshold TH and rising near 41 degrees Celsius defined by International Electrotechnical Commission (at eight minutes after the start of main scanning in FIG. 5).

The composition of the MRI apparatus according to another embodiment of the invention will now be explained. In this further embodiment, a material that changes color with temperature is affixed on a predefined wall in the imaging space 13 and an image of the color condition of the material is taken to determine the change of the temperature in the imaging space 13.

At first, the composition of the MRI apparatus according to the further embodiment will be explained by referring to FIG. 7. In addition, the parts of the composition of the MRI apparatus according to the further embodiment that are substantially the same as the composition of the MRI apparatus according to the embodiment of FIG. 1 will be skipped and the points that are different from the embodiment of FIG. 1 will be described in detail.

As previously described, in the further embodiment, a thermo label as a material that changes color with temperature is affixed on a predefined wall in the imaging space 13, and the normal camera 14 takes an image of the color condition of the thermo label, and the judging unit 16 judges whether imaging space 13 has a point at a temperature greater than the threshold TH by evaluating the image of the thermo label.

Figure 7:
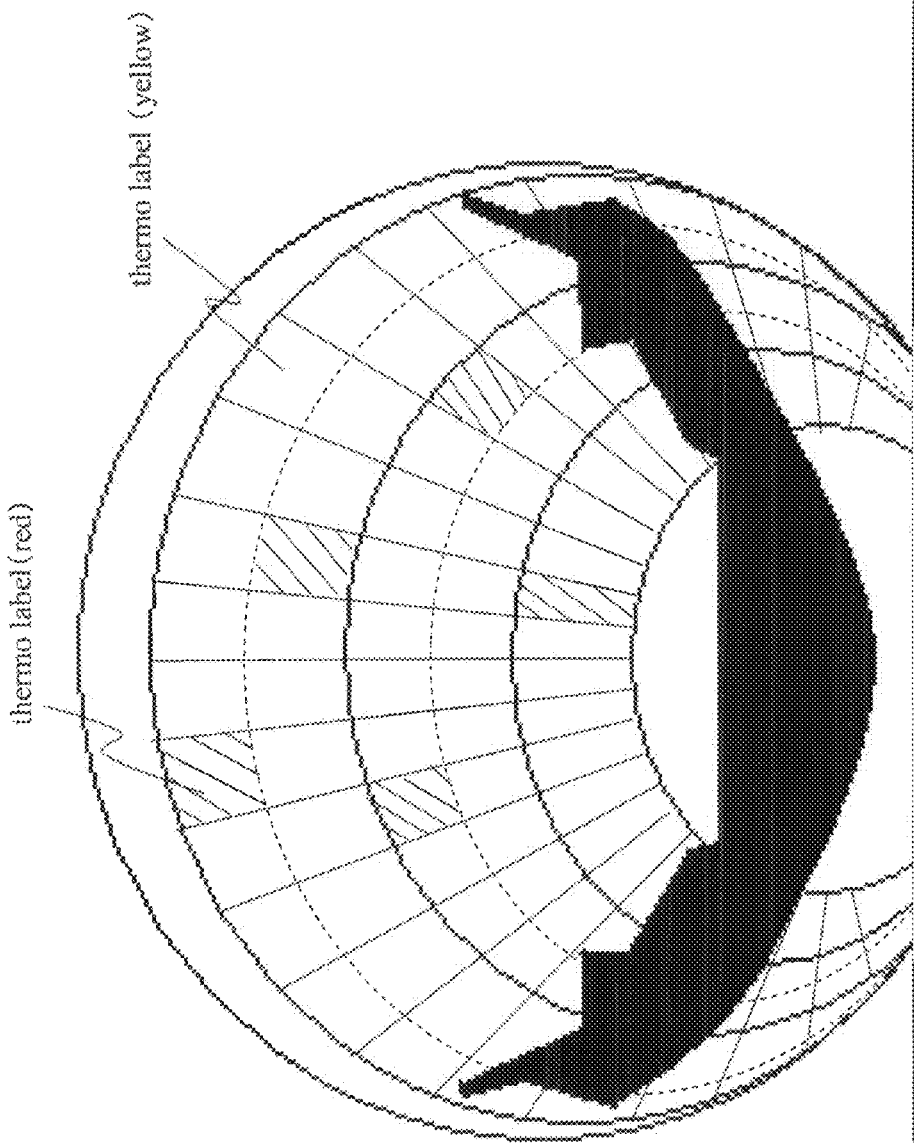
FIG. 7 is an example showing a condition of imaging an imaging space that has affixed thereto thermo labels or thermo paint to the inside wall plan according to a second embodiment of the invention.

The thermo label is affixed on a predefined point in the imaging space 13 to generate an image as shown in FIG. 7. A thermo label that changes color with temperature reversibly is more favorable than one that changes color with temperature irreversibly, for the benefit of not needing a recovering or replacement operation and for cutting costs, but a thermo label that changes color with temperature irreversibly can be used in this embodiment. A thermo label that includes both a part that changes color with temperature reversibly and a part that changes color with temperature irreversibly can also be used.

As previously described, it is preferred that the temperature for the thermo label changing colors is less than or equal to 40 degrees Celsius under the regulation of International Electrotechnical Commission.

For example, the color of the thermo label is yellow under normal conditions, and when the surface temperature of the surface to which the thermo label is affixed changes to 40 degrees Celsius, the color of the thermo label changes to red.

FIG. 7 is an example showing the condition of an image of the imaging space that has affixed thereto thermo labels to the inside wall according to this embodiment of the invention.

The normal camera 14 takes an image of the imaging space 13 after start of main scanning as shown in FIG. 7 and inputs the image to the judging unit 16.

The judging unit 16 recognizes the color of the thermo labels that are affixed in the imaging space 13 based on the image from the normal camera 14 input and judges whether in the imaging space 13 the thermo label has changed from yellow color to red color to indicate show that the surface temperature of the surface to which the thermo label is affixed exceeds 40 degrees Celsius.

As previously described, in this embodiment, the thermo label as the material that changes color with temperature is affixed on a predefined wall in the imaging space 13, but the material is not limited to a thermo label and a liquid material that changes color with temperature, for example a thermo paint, could also be affixed on the predefined wall in the imaging space 13.

Regarding the MRI apparatus composed as above, the sequence to detect the thermo label's color change that is affixed in the imaging space 13 including the subject P will be explained by referring to FIG. 1 through FIG. 8.

FIG. 8 is a flowchart showing a process sequence of the MRI apparatus according to this further embodiment of the invention.

In Step S21 in FIG. 8, the operator slides the tabletop 121 of the bed device 12 that has subject P into the imaging space 13 and places the scanning point of the subject P to a predetermined position in the scanning field. The operator directs the control unit 18 to start the main scanning by the operating unit 10. The control unit 18 directs each unit to start the main scanning based on the direction, and then the apparatus scans a desired some cross section in the scanning field. The image data producing unit 9 then reconstructs the MR signal and produces the image data.

In Step S22 in FIG. 8, the normal camera 14 starts taking the image of the imaging space 13 including the subject P, when the main scanning starts. The normal camera 14 inputs the image to the judging unit 16.

In Step S23 in FIG. 8, the judging unit 16 detects the thermo label's or thermo paint's color change that is affixed in the imaging space 13 including the subject P based on the image transmitted by the normal camera 14.

In Step S24 in FIG. 8, the judging unit 16 judges whether in the imaging space 13 the thermo label or thermo paint has changed to red color showing that the surface temperature of the surface to which the thermo label or thermo paint is affixed exceeds 40 degrees Celsius as the threshold TH.

In Step S25 in FIG. 8, in the case that the judging unit 16 judges that in the imaging space 13 the thermo label or thermo paint has changed to red color (Yes in Step S24), the control unit 18 directs the sequencer 8 to stop the sequence. The sequencer 8 then stops the sequence based on the direction that the control unit 18 transmitted.

According to this first embodiment of the invention, it is possible to detect the change in temperature of the imaging space 13 in the MRI apparatus.

According to this further embodiment of the invention, it is possible for the subject P to recognize the change in temperature of the imaging space 13 visually and it is possible to prevent the subject P from touching the high temperature point in the imaging space 13 by mistake.

Obviously, numerous modifications and variations of the present invention are possible in light of the above teachings. It is therefore to be understood that within the scope of the appended claims, the invention may be practiced otherwise than as specifically described herein.

The invention claimed is:

1. A magnetic resonance imaging apparatus comprising:
a static magnetic field generating unit configured to generate a static magnetic field to a subject inserted into an imaging space;
a gradient magnetic field generating unit configured to generate a gradient magnetic field to the subject;
a transmitting unit configured to transmit a radio frequency pulse to the subject to generate a nuclear magnetic resonance signal;
an image data producing unit configured to generate a tomographic image of the subject based on the nuclear magnetic resonance signal;

a detecting unit configured to detect a change in temperature in the imaging space from outside of the imaging space;

a judging unit configured to judge whether the imaging space has a point at a temperature greater than a threshold; and a controller configured to control the gradient magnetic field generating unit to stop generating the gradient magnetic field to the subject in the case that the judging unit judges the imaging space has a point at a temperature greater than the threshold;

wherein the detecting unit includes a thermographic imaging unit, and the thermographic imaging unit outputs an image that changes in color with changes in temperature, the image showing the change in temperature of the imaging space including the subject; and wherein the judging unit calculates a difference value between a first image and a second image, the first image and the second image being taken at predetermined time intervals by the thermographic imaging unit, and recognizes an increase in temperature; and the control unit controls the gradient magnetic field generating unit to stop generating the gradient magnetic field to the subject in the case that the increase in temperature exceeds the threshold.

2. The magnetic resonance imaging apparatus according to claim 1, wherein the judging unit judges whether the image has a point at a temperature greater than the threshold every predetermined time interval.

3. The magnetic resonance imaging apparatus according to claim 1, further comprising:

a normal imaging unit configured to take an image in an imaging area, the imaging area overlapping an imaging area of the thermographic imaging unit;

an image composing unit configured to combine a first image of change in temperature and a first normal image and combines a second image of change in temperature and a second normal image, wherein the first image of change in temperature and the second image of change in temperature are taken by the thermographic imaging unit and the first normal image and the second normal image are taken by the normal imaging unit, and wherein the first image of change in temperature corresponds to the first normal image and the second image of change in temperature corresponds to the second normal image on the imaging time; and a display unit configured to display a first composite image and a second composite image on a display screen at a same time.

4. The magnetic resonance imaging apparatus according to claim 1, wherein the gradient magnetic field generating unit includes respective gradient coils that correspond to an X-axis direction, a Y-axis direction, and a Z-axis direction in the imaging space, to generate the gradient magnetic field to each of the directions; and the judging unit specifies a coverage area depending on the gradient coil used by the gradient magnetic field generating unit, and the judging unit judges whether the coverage area of the image has a point at a temperature greater than the threshold.

5. The magnetic resonance imaging apparatus according to claim 1, wherein the detecting unit includes a normal imaging unit, and the normal imaging unit takes a normal image of a thermo material that changes color with a surface temperature of the imaging space to which the thermo material is affixed.

6. The magnetic resonance imaging apparatus according to claim 5, wherein the thermo material is a thermo label or a thermo paint.

7. The magnetic resonance imaging apparatus according to claim 5, wherein the judging unit judges whether the image of the thermo material has a point at a temperature greater than the threshold every predetermined time interval.

8. The magnetic resonance imaging apparatus according to claim 5, further comprising:

a display unit configured to display the normal image of the material.

9. The magnetic resonance imaging apparatus according to claim 5, wherein the gradient magnetic field generating unit includes respective gradient coils that correspond to an X-axis direction, a Y-axis direction, and a Z-axis direction in the imaging space to generate the gradient magnetic field to each of the directions; and the judging unit specifies a coverage area depending on the gradient coil used by the gradient magnetic field generating unit, and the judging unit judges whether the coverage area of the image has a point at a temperature greater than the threshold.

10. A magnetic resonance imaging apparatus, comprising:

a static magnetic field generating unit configured to generate a static magnetic field to a subject inserted into an imaging space;

a gradient magnetic field generating unit configured to generate a gradient magnetic field to the subject;

a transmitting unit configured to transmit a radio frequency pulse to the subject to generate a nuclear magnetic resonance signal;

an image data producing unit configured to generate a tomographic image of the subject based on the nuclear magnetic resonance signal;

a detecting unit configured to detect a change in temperature in the imaging space from outside of the imaging space;

a judging unit configured to judge whether the imaging space has a point at a temperature greater than a threshold;

a controller configured to control the gradient magnetic field generating unit to stop generating the gradient magnetic field to the subject in the case that the judging unit judges the imaging space has a point at a temperature greater than the threshold;

wherein the detecting unit includes a thermographic imaging unit, and the thermographic imaging unit outputs an image that changes in color with changes in temperature, the image showing the change in temperature of the imaging space including the subject; and further comprising:

a normal imaging unit configured to take an image in an imaging area, the imaging area overlapping an imaging area of the thermographic imaging unit;

an image composing unit configured to combine the images by the normal imaging unit and the thermographic imaging unit; and a display unit configured to display a composite of the combined images.

11. A magnetic resonance imaging apparatus, comprising:
a static magnetic field generating unit configured to generate a static magnetic field to a subject inserted into an imaging space;
a gradient magnetic field generating unit configured to generate a gradient magnetic field to the subject;
a transmitting unit configured to transmit a radio frequency pulse to the subject to generate a nuclear magnetic resonance signal;
an image data producing unit configured to generate a tomographic image of the subject based on the nuclear magnetic resonance signal;
a detecting unit configured to detect a change in temperature in the imaging space from outside of the imaging space;
a judging unit configured to judge whether the imaging space has a point at a temperature greater than a threshold; and
a controller configured to control the gradient magnetic field generating unit to stop generating the gradient magnetic field to the subject in the case that the judging unit judges the imaging space has a point at a temperature greater than the threshold;
wherein the detecting unit includes a normal imaging unit, and the normal imaging unit takes a normal image of a thermo material that changes color with a surface temperature of the imaging space to which the thermo material is affixed;
wherein the judging unit calculates the difference value between a first image and a second image, the first image and the second image being taken at predetermined time intervals by the thermographic imaging unit, and recognizes the increase in temperature; and
the control unit controls the gradient magnetic field generating unit to stop generating the gradient magnetic field to the subject if an increase in temperature exceeds a predefined value.

12. A magnetic resonance imaging apparatus comprising:
a static magnetic field generating unit configured to generate a static magnetic field in an imaging space into which a subject is placed;
a gradient magnetic field generating unit configured to generate a gradient magnetic field to the subject;
a transmitting unit configured to transmit a radio frequency pulse to the imaging space;
an image data producing unit configured to make a tomographic image of the subject based on a nuclear magnetic resonance signal;
a detecting unit configured to detect a change in temperature in the imaging space from outside of the imaging space; and
a display unit configured to display information related to the change in temperature of the imaging space;
wherein the detecting unit includes a thermographic imaging unit, and the thermographic imaging unit outputs an image that changes in color with changes in temperature, the image showing the change in temperature of the imaging space including the subject; and
further comprising:
a normal imaging unit that takes an image in an imaging area, the imaging area overlapping an imaging area of the thermographic imaging unit;
an image composing unit that combines the images by the normal imaging unit and the thermographic imaging unit; and
wherein the display unit displays a composite of the combined images.

13. The magnetic resonance imaging apparatus according to claim 12,
wherein the gradient magnetic field generating unit includes respective gradient coils that correspond to an X-axis direction, a Y-axis direction, and a Z-axis direction in the imaging space, to generate the gradient magnetic field to each of the directions; and
the judging unit specifies a coverage area depending on the gradient coil used by the gradient magnetic field generating unit, and the judging unit judges whether the coverage area of the image has a point at a temperature greater than the threshold.

14. The magnetic resonance imaging apparatus according to claim 13,
wherein the detecting unit includes a normal imaging unit, and the normal imaging unit takes a normal image of a thermo material that changes color with a surface temperature of the imaging space to which the thermo material is affixed.

15. The magnetic resonance imaging apparatus according to claim 14,
wherein the thermo material is a thermo label or a thermo paint.

16. The magnetic resonance imaging apparatus according to claim 14,
wherein the gradient magnetic field generating unit includes respective gradient coils that correspond to an X-axis direction, a Y-axis direction, and a Z-axis direction in the imaging space to generate the gradient magnetic field to each of the directions; and
the judging unit specifies a coverage area depending on the gradient coil used by the gradient magnetic field generating unit, and the judging unit judges whether the coverage area of the image has a point at a temperature greater than the threshold.

* * * * *